(12) United States Patent
Servidio (10) Patent No.: US 7,413,577 B1
(45) Date of Patent: Aug. 19, 2008

(54) TOTAL STABILIZED KNEE PROSTHESIS WITH CONSTRAINT

(75) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 267 days.

(21) Appl. No.: 11/233,457

(22) Filed: Sep. 22, 2005

(51) Int. Cl.
    *A61F 2/38* (2006.01)
(52) U.S. Cl. ............................ 623/20.14; 623/20.27
(58) Field of Classification Search ............ 623/13.12, 623/18.11, 20.14–20.32
    See application file for complete search history.

(56) References Cited

U.S. PATENT DOCUMENTS

| | | |
|---|---|---|
| 3,748,662 A | 7/1973 | Helfet |
| 4,261,064 A | 4/1981 | Helfet |
| 4,888,021 A | 12/1989 | Forte et al. |
| 4,944,756 A | 7/1990 | Kenna |
| 5,011,496 A | 4/1991 | Forte et al. |
| 5,011,498 A | 4/1991 | Forte et al. |
| 5,059,216 A | 10/1991 | Winters |
| 5,071,438 A | 12/1991 | Jones et al. |
| 5,147,405 A | 9/1992 | Van Zile et al. |
| 5,192,328 A | 3/1993 | Winters |
| 5,219,362 A | 6/1993 | Tuke et al. |
| 5,236,461 A | 8/1993 | Forte |
| 5,282,870 A | 2/1994 | Moser et al. |
| 5,395,401 A | 3/1995 | Bahler |
| 5,871,546 A | 2/1999 | Colleran et al. |
| 5,879,394 A | 3/1999 | Ashby et al. |
| 5,935,173 A | 8/1999 | Roger et al. |
| 5,964,808 A | 10/1999 | Blaha et al. |
| 6,013,103 A | 1/2000 | Kaufman et al. |
| 6,203,576 B1 | 3/2001 | Afriat et al. |
| 6,325,828 B1 | 12/2001 | Dennis et al. |
| 6,406,497 B2 | 6/2002 | Takei |
| 6,494,915 B1 | 12/2002 | Villar Gonzalez et al. |
| 2004/0243244 A1 * | 12/2004 | Otto et al. ............... 623/20.27 |

OTHER PUBLICATIONS

Iwaki, H. et al, "Tibiofemoral movement 1: The shapes and relative movements of the femur and tibia in the unloaded cadaver knee," *J Bone Joint Surg (Br)*, 2000:82-B, 1189-95.

(Continued)

*Primary Examiner*—Thomas J Sweet
*Assistant Examiner*—Jonathan R Stroud
(74) *Attorney, Agent, or Firm*—Arthur Jacob (57) ABSTRACT

An improvement in a total stabilized knee prosthesis wherein stabilization against uncontrolled relative rotation between a femoral component and a tibial component about a longitudinal axis, during articulation of the knee prosthesis, is attained by the engagement of a femoral stabilizing compartment with a tibial stabilizing post, the improvement including profile contour configurations on inner surface portions of condylar surfaces and on corresponding outer surface portions of tibial articular surfaces, the profile contour configurations being flared outwardly, in directions away from an intermediate sagittal plane, along posterior aspects of the condylar surfaces and the tibial articular surfaces engaged through deep flexion for providing an engagement between the profile contour configurations sufficient to establish a desired level of constraint against relative rotational movement between the femoral component and the tibial component about the longitudinal axis enabling a decrease in the level of constraint provided by the engagement between the post and the compartment during articulation through deep flexion.

12 Claims, 7 Drawing Sheets

OTHER PUBLICATIONS

Hill, P.F. et al, "Tibiofemoral movement 2: The loaded and unloaded living knee studied by MRI," *J Bone Joint Surg* (*Br*), 2000: 82-B, 1196-8.

Nakagawa, S. et al, "Tibiofemoral movement 3: Full flexion in the living knee studied by MRI," *J Bone Joint Surg* (*Br*), 2000:82-B, 1199-2000.

Karrholm, J. et al, "Tibiofemoral movement 4: Changes of axial tibial rotation caused by forced rotation at the weight-bearing knee studied by RSA," *J Bone Joint Surg* (*Br*), 2000:82-B, 1201-3.

Wright Medical Technology, Inc., "Advance Knee System, Medial—Pivot Knee," 1-5.

Wright Medical Technology, Inc., "Advance Knee System, Traditional, Medial—Pivot, Posterior Stabilized," 1-8.

Pinskerova, V. et al, "The shapes and relative movements of the femur and tibia in the unloaded cadaveric knee: A study using MRI as an anatomic tool."

Howmedica Inc., "Duracon, the Femoral System," 1994, p. 5.

Howmedica Inc., "Duracon, the Tibial System," 1994, p. 7.

Stryker Howmedica Osteonics, "Duracon PS, Posteriorly Stabilized Total Knee System."

Stryker Howmedica Osteonics, "Duracon CR, Cruciate Retaining Total Knee System."

Enclosed are two Forms PTO/SB/08A and two Froms PTO/SB/08B which contains a separate list of the references. Only copies of the publications are enclosed. The U.S. patents are not submitted herewith, in accordance with the notice in the United States Patent and Trademark Office *OG Notices:* Aug. 5, 2003.

Iwaki, H. et al, "Tibiofemoral movement 1: The shapes and relative movements of the femur and tibia in the unloaded cadaver knee," J Bone Joint Surg (Br), 2000:82-B, 1189-95.

Hill, P.F. et al, "Tibiofemoral movements 2: The loaded and unloaded living knee studied by MRI," J Bone Joint Surg (Br), 2000:82-B, 1196-8.

Nakagawa, S. et al, "Tibiofemoral movement 3: Full flexion in the living knee studied by MRI," J Bone Joint Surg (Br), 2000:82-B, 1199-2000.

Karrholm, J. et al, "Tibiofemoral movement 4: Changes of axial tibial rotation caused by forced rotation . . . " J Bone Joint Surg (Br), 2000:82-B, 1199-2000.

Wright Medical Technology, Inc., "Advanced Knee System, Medial—Pivot Knee," 1-5.

Wright Medical Technology, Inc., "Advance Knee System, Traditional, Medial—Pivot, Posterior Stabilized," 1-8.

Pinskerova, V. et al, "The shapes and relative movements of the femur and tibia in the unloaded cadaveric knee: A study using MRI as an anatomic tool."

Howmedica Inc., "Duracon, the Femoral System," 1994, p. 5.

Howmedica Inc., "Duracon, the Tibial System," 1994, p. 7.

Stryker Howmedica Osteonics, "Duracon PS, Posteriorly Stabilized Total Knee System."

Stryker Howmedica Osteonics, "Duracon CR, Cruciate Retaining Total Knee System."

\* cited by examiner

FIG. 1              FIG. 2

0° FLEXION

90° FLEXION
FIG. 6

100° FLEXION

150° FLEXION

TOTAL STABILIZED KNEE PROSTHESIS WITH CONSTRAINT

The present invention relates generally to the replacement of a natural knee joint with a knee prosthesis and pertains, more specifically, to addressing deficiencies in soft tissue and, in particular, ligaments with a total stabilized knee prosthesis which provides requisite stability and improved soft tissue balance, together with extended longevity.

The natural knee joint includes distal femoral and proximal tibial articular surfaces which have an anatomical relationship and placement maintained by soft tissue and, in particular, ligaments during articulation of the knee joint. The posterior cruciate, anterior cruciate, medial collateral and lateral collateral ligaments assist in stabilizing the knee during flexion. Relative rotation between the femur and the tibia, and femoral rollback are controlled by ligaments during knee flexion.

The soft tissue and, in particular, ligaments can become compromised as a result of injury or disease. For example, arthritis can damage the knee articular surfaces thereby producing a malaligned knee joint which stresses soft tissue, resulting in soft tissue laxity and concomitant damage to ligaments. Such conditions present a challenge to an orthopedic surgeon whose objective is to provide a patient with a stable knee, despite the presence of compromised soft tissue.

Posterior stabilized prosthetic knee joints have been available to address posterior ligament deficiency. Most posterior stabilized knee prostheses enable relative rotation between the femur and the tibia during flexion, with stability to prevent femoral anterior subluxation. For example, reaction forces occurring during such activities as stair descending effect anterior and posterior movements of the knee which tend to induce femoral anterior subluxation. In order to prevent femoral anterior subluxation, posterior stabilized knee prostheses are provided with femoral cam surfaces engaged by tibial post follower surfaces to preclude relative movements between the femur and the tibia which otherwise could result in femoral anterior subluxation.

Total stabilized prosthetic knee joints are available to address posterior cruciate ligament deficiency coupled with collateral ligament deficiency. Most total stabilized knee prostheses offer a reduced range of relative rotation between the femur and the tibia during flexion, while providing stability to prevent femoral anterior subluxation, with limited varus-valgus movement. Varus-valgus movements of the knee usually are the result of medial and lateral ground reaction forces which occur during such activities as walking. Again, femoral anterior subluxation usually is prevented by the engagement of femoral cam surfaces with tibial post follower surfaces to preclude relative movements between the femur and the tibia which otherwise could result in femoral anterior subluxation. The femoral cam surfaces usually are located within a compartment in the distal femoral component, while the follower surfaces on the tibial post of the proximal tibial component engage the cam surfaces provided by the compartment. The reduced range of relative rotation between the femur and the tibia, and limited varus-valgus movement, are controlled by the relative medial/lateral width of the femoral compartment and the tibial post which extends into the femoral compartment.

Current posterior stabilized knee prostheses and total stabilized knee prostheses do not address all of the various issues presented by patients with compromised soft tissue conditions requiring different reconstructive surgical responses to attain soft tissue balancing. Consequently, surgical compromises become necessary, and such compromises can lead to negative clinical results.

The present invention provides total stabilized knee prostheses with constraint in levels which better address soft tissue balancing needs encountered among patients having various compromised soft tissue conditions. As such, the present invention attains several objects and advantages, some of which are summarized as follows: Enables a better surgical response to a wider variety of conditions encountered in patients who require a prosthetic knee and who have compromised soft tissue at the knee; allows a surgeon to select a knee prosthesis which best addresses the particular needs of a patient with compromised soft tissue at the knee; provides a total stabilized knee prosthesis offering constraint capable of accommodating any of a variety of soft tissue conditions encountered in different patients; enables a total stabilized knee prosthesis to better withstand stresses arising during the provision of constraint which addresses conditions presented by compromised soft tissue at the site of the prosthetic knee; reduces stresses at the articular surfaces of a total knee prosthesis for decreased wear and increased longevity; provides a total stabilized knee prosthesis capable of exemplary performance over an extended service life.

The above objects and advantages, as well as further objects and advantages, are attained by the present invention which may be described briefly as providing, in a total stabilized knee prosthesis for implantation to replace a natural knee joint, the knee prosthesis having a femoral component including at least one condylar element with a condylar surface having a transverse axis of rotation extending transverse to a sagittal plane, and a tibial component including at least one articular surface configured for engagement with the condylar surface of the femoral component during articulation of the knee prosthesis about the transverse axis of rotation, with the condylar surface and the articular surface engaged along corresponding posterior aspects during deep flexion, the condylar surface and the articular surface being configured and dimensioned for enabling engagement between the condylar surface and the articular surface along a prescribed track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation, and wherein a level of constraint against uncontrolled relative rotational movement and varus-valgus movements between the femoral component and the tibial component is provided by engagement of a post on one of the femoral component and the tibial component with a compartment in the other of the femoral component and the tibial component: an improvement wherein the inner surface portion and the outer surface portion are flared outwardly, in a direction away from the sagittal plane, along the posterior aspects of the condylar surface and the articular surface for providing an engagement between the profile contour configurations sufficient to establish a level of constraint against uncontrolled relative rotational movement between the femoral component and the tibial component about the longitudinal axis enabling a decrease in the level of constraint provided by the engagement between the post and the compartment during articulation through deep flexion.

In addition, the present invention provides, in a total stabilized knee prosthesis for implantation to replace a natural knee joint, the knee prosthesis having a femoral component including a lateral condylar element and a medial condylar element, each condylar element including a condylar surface having a transverse axis of rotation extending transverse to a sagittal plane, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during deep flexion, each condylar surface and each articular surface being configured and dimensioned for enabling engagement between the condylar surfaces and corresponding articular surfaces along respective prescribed tracks each having a predetermined curvature which enable relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation, and wherein a level of constraint against uncontrolled relative rotational movement and varus-valgus movements between the femoral component and the tibial component is provided by engagement of a post on one of the femoral component and the tibial component with a compartment in the other of the femoral component and the tibial component: an improvement wherein the inner surface portions and the outer surface portions are flared outwardly, in a direction away from the sagittal plane, along the posterior aspects of the condylar surfaces and articular surfaces for providing an engagement between the profile contour configurations sufficient to establish a level of constraint against uncontrolled relative rotational movement between the femoral component and the tibial component about the longitudinal axis enabling a decrease in the level of constraint provided by the engagement between the post and the compartment during articulation through deep flexion.

The invention will be understood more fully, while still further objects and advantages will become apparent, in the following detailed description of preferred embodiments of the invention illustrated in the accompanying drawing, in which.

Figure 1:
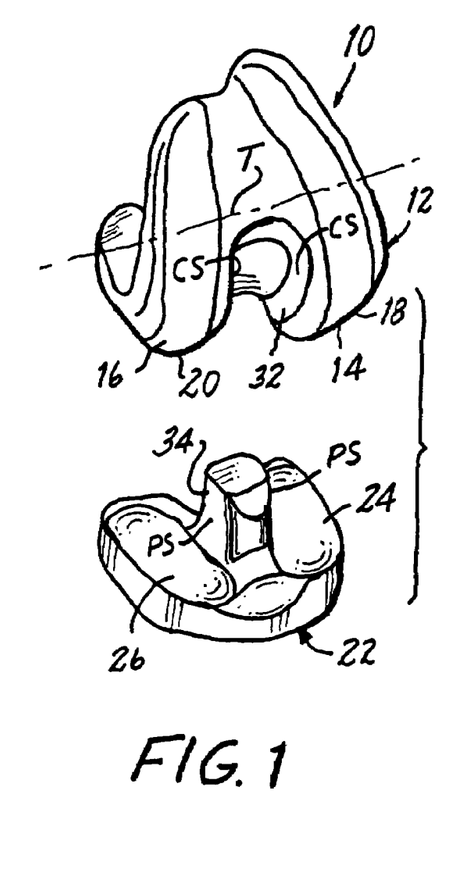
FIG. 1 is an exploded perspective view showing portions of a knee prosthesis constructed in accordance with the present invention.
Figure 2:
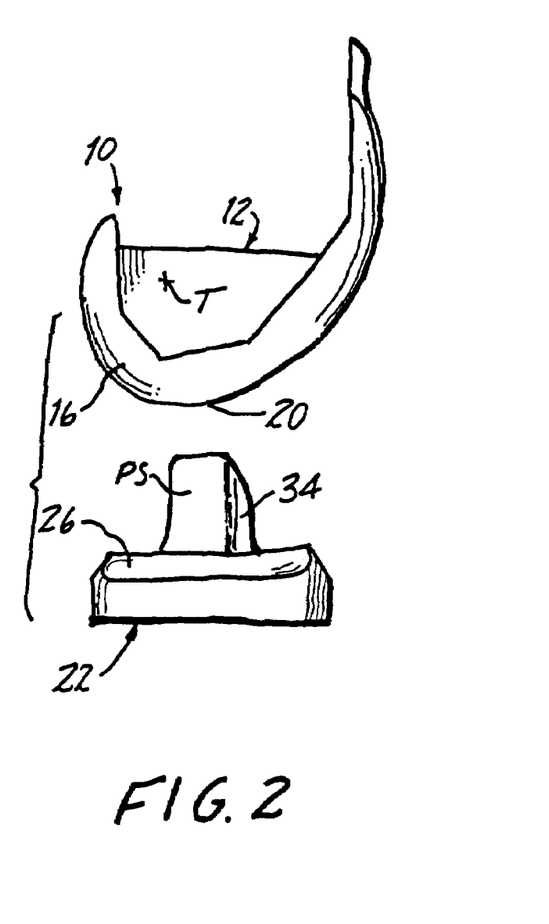
FIG. 2 is an exploded side elevational view of the portions of the knee prosthesis.

Referring now to the drawing, and especially to FIGS. 1 and 2 thereof, a total stabilized knee prosthesis constructed in accordance with the present invention is shown at 10 and is seen to comprise a femoral component 12 having condylar elements illustrated in the form of condyles including a lateral condyle 14 and a medial condyle 16. Each condyle 14 and 16 includes a condylar surface 18 and 20, respectively. A tibial component 22 has articular surfaces including a lateral articular surface 24 for engagement with lateral condylar surface 18 of lateral condyle 14, and a medial articular surface 26 for engagement with medial condylar surface 20 of medial condyle 16, for rotation about a transverse axis of rotation T.

In the total knee replacement provided by knee prosthesis 10, the posterior cruciate ligament has been sacrificed. The collateral ligaments of the recipient of the knee prosthesis 10 have been compromised and are deficient, and knee prosthesis 10 includes a stabilizing mechanism for stabilizing the engagement between the lateral condyle 14 and the lateral articular surface 24, and between the medial condyle 16 and the medial articular surface 26, during articulation of the knee prosthesis 10 within the range of articulation in which the posterior cruciate ligament and the collateral ligaments ordinarily would provide stability in the natural knee. The stabilizing mechanism includes a stabilizing compartment 32 on the femoral component 12, between the condyles of the femoral component 12, the compartment 32 preferably being located intermediate the lateral condyle 14 and the medial condyle 16 of the femoral component 12, and a stabilizing post 34 on the tibial component 22, between the articular surfaces of the tibial component 22, the post 34 preferably being located intermediate the lateral articular surface 24 and the medial articular surface 26 of the tibial component 22, for projecting in a superior direction into the stabilizing compartment 32, in a manner known in posterior stabilized prosthetic knee implants.

Figure 3:
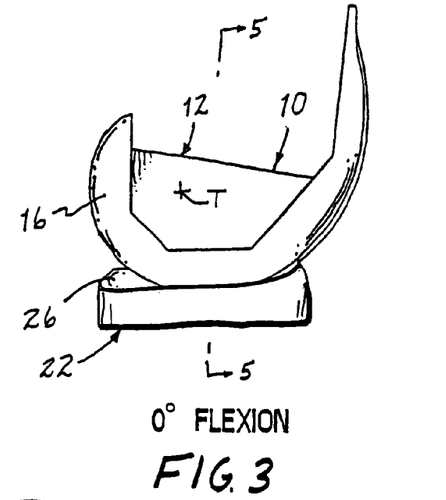
FIG. 3 is a side elevational view of the portions of the knee prosthesis showing the femoral component engaged with the tibial component, at 0° of flexion.
Figure 4:
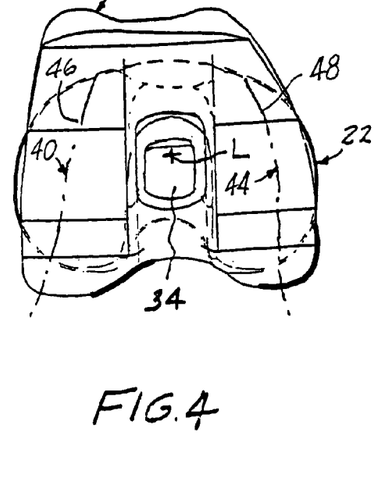
FIG. 4 is a partially diagrammatic top plan view of the prosthesis in the position shown in FIG. 3.
Figure 5:
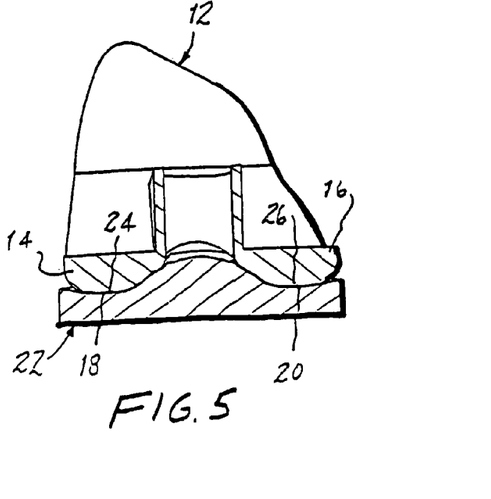
FIG. 5 is a cross-sectional view taken along line 5-5 of FIG. 3.
Figure 6:
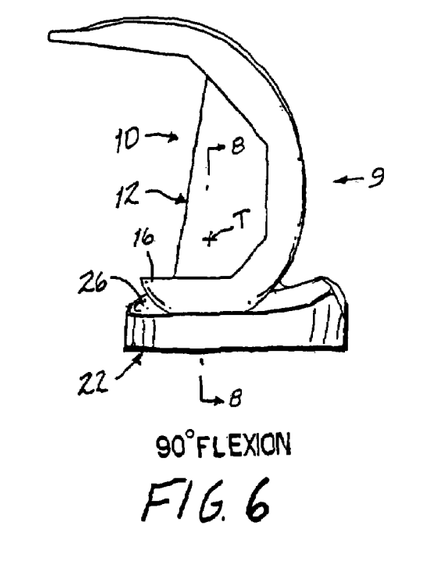
FIGS. 6, 7 and 8 are views similar to FIGS. 3, 4 and 5, respectively, but showing the components at 90° of flexion.
Figure 7:
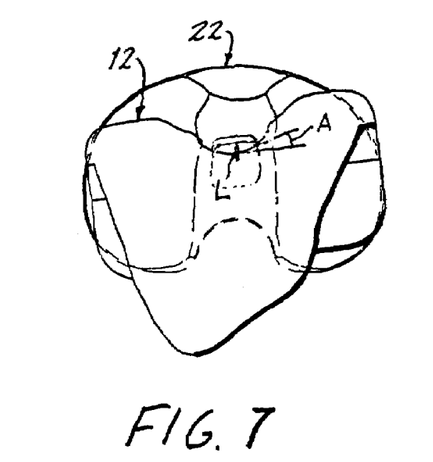
Figure 8:
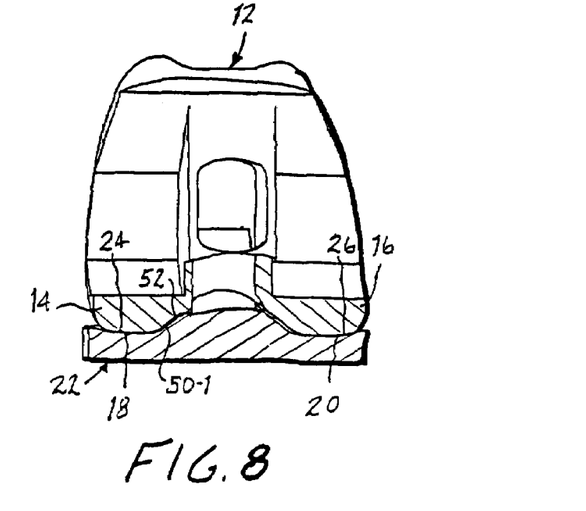
Figure 18:
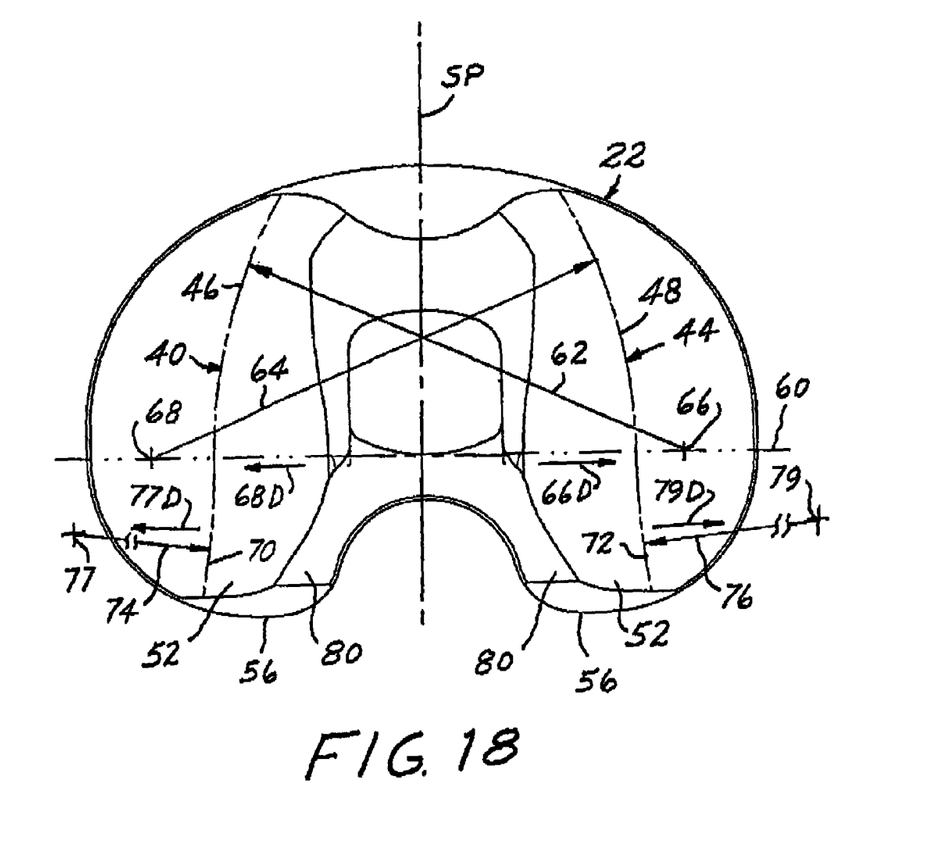
FIG. 18 is an enlarged diagrammatic top plan view showing the articular surfaces of the tibial component of the knee prosthesis.

Turning now to FIGS. 3 through 9, viewed in conjunction with FIG. 18, knee prosthesis 10 is illustrated at 0° of flexion, or full extension, in FIGS. 3 through 5, and at 90° of flexion in FIGS. 6 through 9, and the condylar surfaces of the condyles of the femoral component 12 are engaged with the articular surfaces of the tibial component 22. The condylar surfaces 18 and 20 and the articular surfaces 24 and 26 are dimensioned and configured such that upon implantation of the knee prosthesis 10, relative rotational movement between the femoral component 12 and the tibial component 22 during articulation of the knee prosthesis 10 essentially emulates the relative rotation observed in the natural knee, between about 0° of flexion and about 90° of flexion. Thus, engagement between lateral condylar surface 18 and lateral articular surface 24 is so complementary, and preferably essentially congruent, as illustrated in FIGS. 5 and 8, by the profile contour configurations in a generally medial-lateral longitudinal plane at positions along a first prescribed track 40 having a predetermined curvature in a generally coronal plane, and engagement between medial condylar surface 20 and medial articular surface 26 is so complementary, and preferably essentially congruent, as illustrated in FIGS. 5 and 8, along a second prescribed track 44 having a predetermined curvature in a generally coronal plane, that the relative configurations of the condylar surfaces 18 and 20 and the articular surfaces 24 and 26 will enable relative rotational movement between the femoral component 12 and the tibial component 22, about a longitudinal axis L, lying in a generally sagittal plane, in such a manner as to emulate the relative rotation observed in the natural knee during articulation about transverse axis of rotation T within the range of flexion from about 0° of flexion to about 90° of flexion. In the preferred construction, tracks 40 and 44 each have a generally arcuate curvature along respective portions 46 and 48 engaged by femoral component 12 during articulation within that range of flexion.

FIGS. 10 through 16, together with FIGS. 3 through 9, illustrate articulation of the knee prosthesis 10 within a range of flexion from about 0° of flexion to about 150° of flexion. During flexion within that range of about 0° of flexion to about 150° of flexion, relative rotation between the femoral component 12 and the tibial component 22 takes place about longitudinal axis L. The total relative rotation reached is depicted by angle A in each of FIGS. 7, 11 and 15. A level of constraint against uncontrolled relative rotation between femoral component 12 and tibial component 22, as provided by engagement between compartment 32 and post 34 as well as by engagement of condylar surfaces 16 and 20 with respective articular surfaces 24 and 26, limits relative rotation between femoral component 12 and tibial component 22 to an angle A of up to about 5°. As described in greater detail below, even during articulation through deep flexion, that is, within the range of about 90° of flexion to about 150° of flexion, where engagement between compartment 32 and post 34 becomes more limited, a sufficient level of constraint is provided to assure that angle A does not exceed about 5°.

Throughout flexion and extension within the range of about 0° of flexion and about 90° of flexion, engagement between lateral condylar surface 18 and lateral articular surface 24 is along generally arcuate portion 46 of track 40 and the relative profile contour configurations maintain the desired essential congruency between the engaged surfaces 18 and 24. Likewise, engagement between the medial condylar surface 20 and the medial articular surface 26 is along generally arcuate portion 48 of track 44 and essential congruency is maintained between the engaged surfaces 20 and 26. The essential congruency assures that contact between the condylar surfaces and the respective articular surfaces is maintained over a maximum area of contact so as to minimize contact stresses and reduce wear on the tibial component 22.

Figure 9:
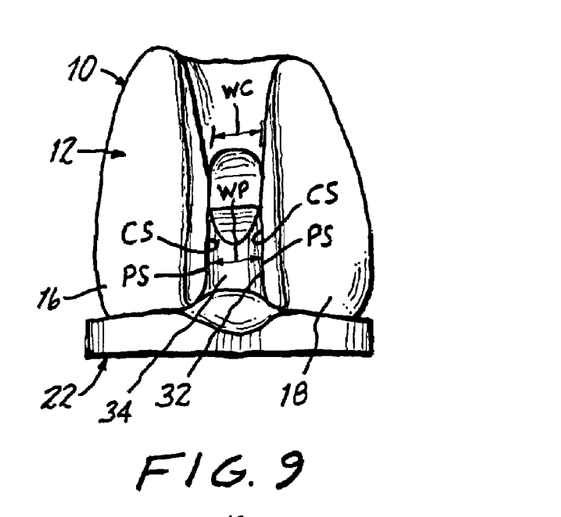
FIG. 9 is a front elevational view taken in the direction of arrow 9 in FIG. 6.
Figure 10:
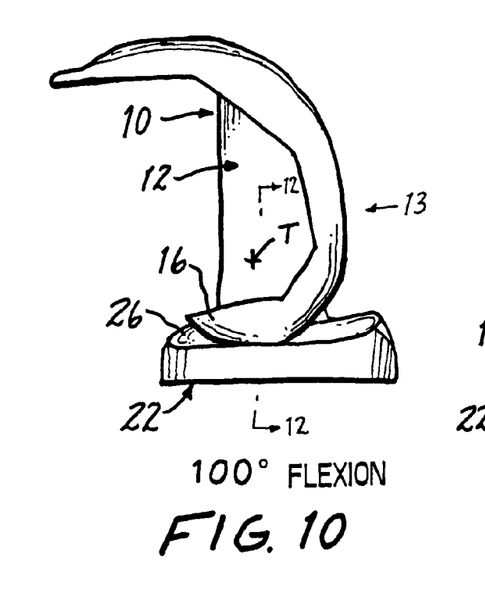
FIGS. 10, 11 and 12 are views similar to FIGS. 6, 7 and 8, respectively, but showing the components at 100° of flexion.
Figure 11:
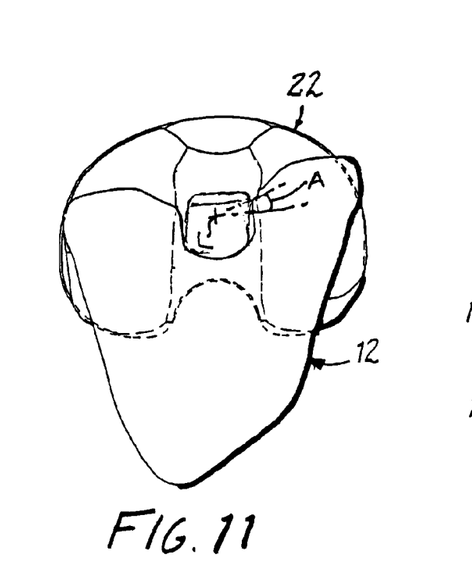
Figure 13:
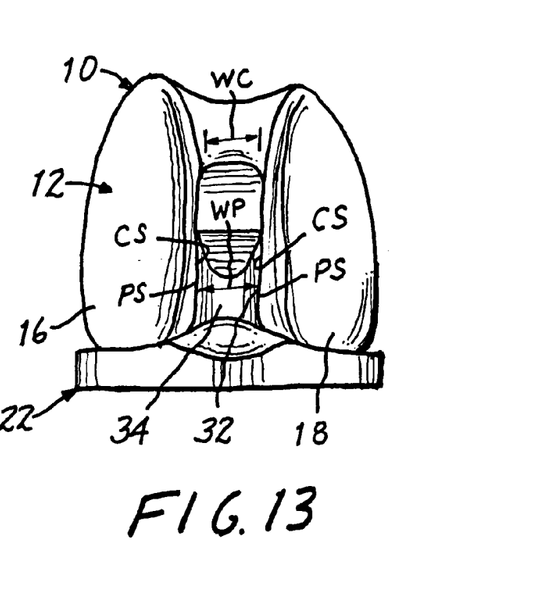
FIG. 13 is a front elevational view taken in the direction of arrow 13 in FIG. 10.
Figure 14:
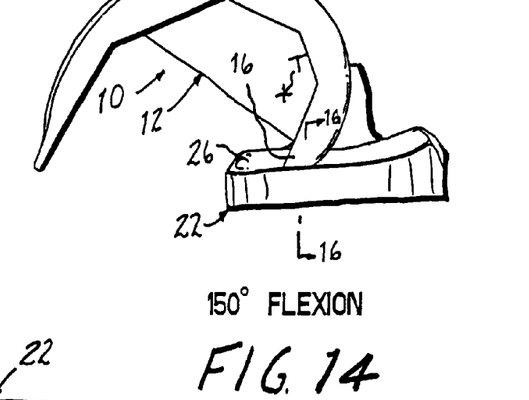
FIGS. 14, 15 and 16 are views similar to FIGS. 6, 7 and 8, respectively, but showing the components at 150° of flexion.
Figure 15:
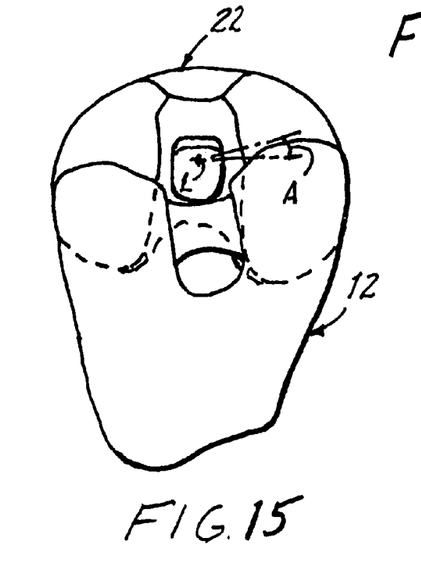

With reference to FIGS. 9 and 13, as well as to FIGS. 1 and 2, constraint against uncontrolled varus-valgus movement is provided by the engagement of stabilizing compartment 32 of femoral component 12 with stabilizing post 34 of tibial component 22. The compartment 32 and the post 34 are configured and dimensioned so that during articulation of knee prosthesis 10 within the range of flexion between about 0° of flexion and about 100° of flexion, engagement between compartment 32 and post 34 limits varus-valgus movement to approximately 2° to 4°. The relative configurations and dimensions provided by medial/lateral width WC between sides CS of the compartment 32 and by medial/lateral width WP between sides PS of post 34 are such that the engagement of sides CS with corresponding confronting sides PS during articulation over the aforesaid range of flexion will preclude varus-valgus movements beyond 2° to 4°. Thus, during such activities as walking, where articulation of knee prosthesis 10 falls within the range of about 0° of flexion and about 100° of flexion, varus-valgus movements induced by ground reaction forces are confined to approximately 2° to 4°, thereby providing stability to knee prosthesis 10 which ordinarily would be provided to a natural knee joint by healthy collateral ligaments. Such constraint against varus-valgus movements during articulation in deep flexion, that is, within a range of flexion beyond about 100° of flexion, and up to about 150° of flexion, is not required since activities within that range of articulation, such as rising from a chair, are accompanied by only limited ground reaction forces.

Figure 12:
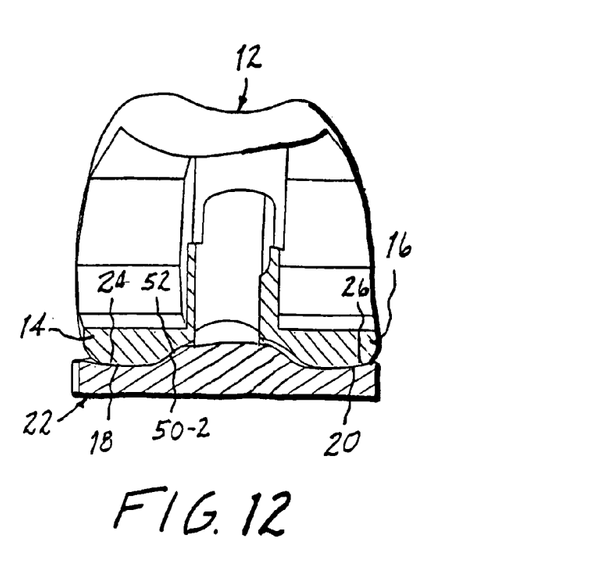
Figure 16:
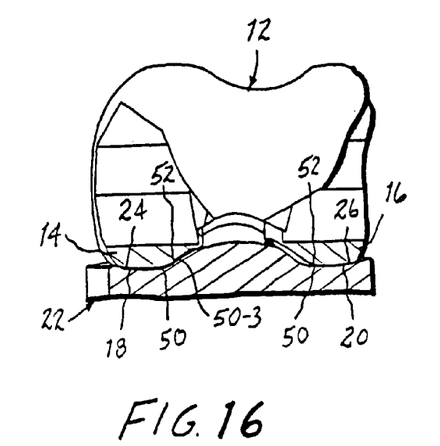
Figure 17:
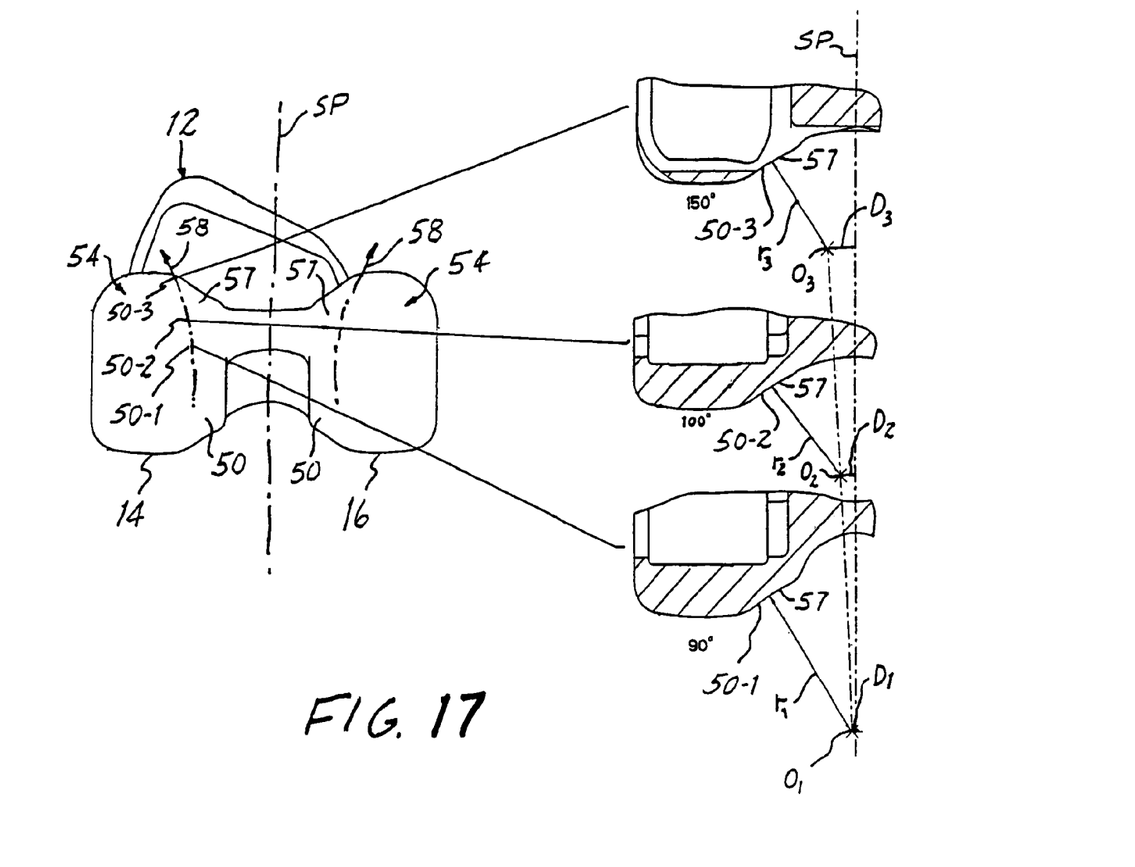
FIG. 17 is an enlarged posterior elevational view showing a posterior aspect of condylar surfaces of the femoral component of the knee prosthesis, together with cross-sectional views taken in generally medial-lateral planes at locations corresponding to about 90°, 100° and 150° of flexion along a condylar surface and showing profile contour configurations at those locations.

As seen in FIGS. 8, 12 and 16, viewed in conjunction with FIG. 17, each condylar surface 18 and 20 includes an inner surface portion 50 which engages a corresponding outer surface portion 52 of a respective articular surface 24 and 26 along corresponding posterior aspects 54 and 56 of the respective inner and outer surface portions 50 and 52, and the inner surface portions 50 are flared outwardly in directions away from an intermediate sagittal plane SP. As illustrated diagrammatically in FIG. 17, a flared surface area 57 extends along each inner surface portion 50 and follows a direction 58 diverging outwardly relative to intermediate sagittal plane SP so as to maintain essential congruency between the profile contour configurations, along the posterior aspects 54 and 56 of the condylar surfaces 18 and 20 and the corresponding articular surfaces 24 and 26. The profile contour configuration of the flared surface area 57 of an inner surface portion 50 is depicted by 50-1 at a location corresponding to 90° of flexion, by 50-2 at a location corresponding to 100° of flexion, and by 50-3 at a location corresponding to 150° of flexion. Each profile contour configuration 50-1, 50-2, and 50-3 has a corresponding radius $r_1$, $r_2$ and $r_3$ extending from a respective origin $O_1$, $O_2$ and $O_3$ spaced outwardly from sagittal plane SP a corresponding distance $D_1$, $D_2$ and $D_3$. Distance $D_2$ is greater than distance $D_1$, and distance $D_3$ is greater than distance $D_2$ so as to accomplish the desired outward flare of the surface area 57. The term "flared", as applied to each inner surface portion 50, is meant to describe a smooth and gradual transition as the inner surface portion 50 follows the direction 58 of surface area 57, as represented in FIG. 17 wherein the origins of the radii of profile contour configurations 50-1, 50-2 and 50-3 are spaced successively farther outwardly from sagittal plane SP. As shown in FIG. 17, the outward flare of the inner surface portions 50 preferably commences at locations on condylar surfaces 18 and 20 corresponding to about 90° of flexion and extends to locations corresponding to about 150° of flexion for maintaining a maximum area of contact between the respective condylar and articular surfaces, thereby minimizing contact stresses and reducing wear on the tibial component 22.

In the preferred construction, the profile contour configurations at 50-1, 50-2 and 50-3 of the inner surface portions 50 are provided with a concave contour along the posterior aspects 54 of the condylar surfaces 18 and 20, as illustrated by the radii of the profile contour configurations, while the outer surface portions 52 are provided with an essentially complementary convex contour along the posterior aspects 56 of the articular surfaces 24 and 26 so as to assure increased areas of contact without decreasing the amount of bearing material available to the tibial component 22 at the articular surfaces 24 and 26.

In order to provide a desired level of constraint against uncontrolled relative rotation between femoral component 12 and tibial component 22 during deep flexion, that is, within the range of articulation between about 90° of flexion and about 150° of flexion, outer surface portions 52 are flared outwardly, in directions away from sagittal plane SP. The outward flare of the outer surface portions 52 preferably commences at locations corresponding to about 90° of flexion, as indicated in FIG. 18 by transverse line 60, and continues to locations corresponding to about 150° of flexion. Each outer surface portion 52 follows the generally arcuate curvature along respective portions 46 and 48 of tracks 40 and 44 from a location corresponding to full extension up to the location depicted by line 60. The generally arcuate portions 46 and 48 each have a radius 62, 64, respectively, extending from a corresponding center 66, 68 lying along transverse line 60, and spaced in a corresponding transverse direction 66D, 68D from sagittal plane SP. The outer surface portions 52 then are flared outwardly to follow respective portions 70 and 72 of tracks 40 and 44, each portion 70 and 72 following a predetermined curvature which preferably is generally arcuate and has a respective radius 74, 76 extending from a corresponding center 77, 79 spaced in a corresponding transverse direction 77D, 79D opposite to respective counterpart transverse directions 66D, 68D so that the contour configurations of outer surface portions 52 along portions 70 and 72 of tracks 40 and 44 are essentially complementary to corresponding contour configurations of inner surface portions 50.

By flaring the outer surface portions 52 outwardly, congruency is increased while increased bearing material is made available to tibial component 22 at portions 80 of tibial component 22 so that bearing material of the tibial component 22 is maintained at a maximum, with a concomitant decrease in bearing stresses and increase in longevity. Moreover, rather than relying upon engagement between stabilizing compartment 32 and stabilizing post 34 to provide the full desired level of constraint against uncontrolled relative rotation between femoral component 12 and tibial component 22, during articulation of knee prosthesis 10 in deep flexion, that is, within the range of about 90° of flexion to about 150° of flexion, a level of constraint is provided by engagement between inner surface portions 50 and outer surface portions 52, sufficient to enable shifting of the forces of constraint, and concomitant stresses of stabilizing contact, from stabilizing post 34 to portions 80 of tibial component 22, where the increased amount of bearing material provided by the outward flare of outer surface portions 52 enables the tibial component 22 to better withstand the stresses imposed by providing the full desired level of constraint against relative rotational movement between femoral component 12 and tibial component 22. In this manner, knee prosthesis 10 is provided with a desired level of constraint for precluding relative rotation between femoral component 12 and tibial component 22 beyond about 5° of relative rotation, during deep flexion.

It will be seen that the present invention attains all of the objects and advantages summarized above, namely: Enables a better surgical response to a wider variety of conditions encountered in patients who require a prosthetic knee and who have compromised soft tissue at the knee; allows a surgeon to select a knee prosthesis which best addresses the particular needs of a patient with compromised soft tissue at the knee; provides a total stabilized knee prosthesis offering constraint capable of accommodating any of a variety of soft tissue conditions encountered in different patients; enables a total stabilized knee prosthesis to better withstand stresses arising during the provision of constraint which addresses conditions presented by compromised soft tissue at the site of the prosthetic knee; reduces stresses at the articular surfaces of a total knee prosthesis for decreased wear and increased longevity; provides a total stabilized knee prosthesis capable of exemplary performance over an extended service life.

It is to be understood that the above detailed description of preferred embodiments of the invention are provided by way of example only. Various details of design and construction may be modified without departing from the true spirit and scope of the invention, as set forth in the appended claims.

The embodiments of the invention in which an exclusive property or privilege is claimed are defined as follows:

1. In a total stabilized knee prosthesis for implantation to replace a natural knee joint, the knee prosthesis having a femoral component including at least one condylar element with a condylar surface having a transverse axis of rotation extending transverse to a sagittal plane, and a tibial component including at least one articular surface configured for engagement with the condylar surface of the femoral component during articulation of the knee prosthesis about the transverse axis of rotation, with the condylar surface and the articular surface engaged along corresponding posterior aspects during deep flexion, the condylar surface and the articular surface being configured and dimensioned for enabling engagement between the condylar surface and the articular surface along a prescribed track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation, and wherein a level of constraint against uncontrolled relative rotational movement and varus-valgus movements between the femoral component and the tibial component is provided by engagement of a post on one of the femoral component and the tibial component with a compartment in the other of the femoral component and the tibial component:

an improvement wherein the inner surface portion and the outer surface portion are each flared outwardly, in a transverse direction away from the sagittal plane, along the posterior aspects of the condylar surface and the articular surface for providing an engagement between the profile contour configurations sufficient to establish a level of constraint against uncontrolled relative rotational movement between the femoral component and the tibial component about the longitudinal axis, thereby enabling a decrease in the level of constraint provided by the engagement between the post and the compartment during articulation through deep flexion.

2. The improvement of claim 1 wherein the flared surface portions extend along the posterior aspects of the condylar surface and the articular surface from locations corresponding to about 90° of flexion to locations corresponding to about 150° of flexion.

3. The improvement of claim 2 wherein the predetermined curvature of the prescribed track includes a first portion extending from a location corresponding to about 0° of flexion up to a location corresponding to about 90° of flexion, the first portion being generally arcuate and having a radius extending from a center spaced in a first transverse direction from the sagittal plane.

4. The improvement of claim 3 wherein the predetermined curvature of the prescribed track includes a second portion extending from a location corresponding to about 90° of flexion to a location corresponding to about 150° of flexion, the second portion being generally arcuate and having a radius extending from a center spaced in a second transverse direction from the sagittal plane, the second transverse direction being opposite to the first transverse direction.

5. The improvement of claim 1 wherein relative rotation about the longitudinal axis of rotation is enabled up to about 5° of relative rotation, during flexion up to about 90° of flexion.

6. The improvement of claim 1 wherein relative rotation about the longitudinal axis of rotation is enabled up to about 5° of relative rotation, during flexion up to about 150° of flexion.

7. In a total stabilized knee prosthesis for implantation to replace a natural knee joint, the knee prosthesis having a femoral component including a lateral condylar element and a medial condylar element, each condylar element including a condylar surface having a transverse axis of rotation extending transverse to a sagittal plane, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during deep flexion, each condylar surface and each articular surface being configured and dimensioned for enabling engagement between the condylar surfaces and corresponding articular surfaces along respective prescribed tracks each having a predetermined curvature which enable relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation, and wherein a level of constraint against uncontrolled relative rotational movement and varus-valgus movements between the femoral component and the tibial component is provided by engagement of a post on one of the femoral component and the tibial component with a compartment in the other of the femoral component and the tibial component:

an improvement wherein the inner surface portions and the outer surface portions are each flared outwardly, in a transverse direction away from the sagittal plane, along the posterior aspects of the condylar surfaces and articular surfaces for providing an engagement between the profile contour configurations sufficient to establish a level of constraint against uncontrolled relative rotational movement between the femoral component and the tibial component about the longitudinal axis, thereby enabling a decrease in the level of constraint provided by the engagement between the post and the compartment during articulation through deep flexion.

8. The improvement of claim 7 wherein the flared surface portions extend along the posterior aspects of the condylar surfaces and the articular surfaces from locations corresponding to about 90° of flexion to locations corresponding to about 150° of flexion.

9. The improvement of claim 8 wherein the predetermined curvature of each prescribed track includes a first portion extending from a location corresponding to about 0° of flexion up to a location corresponding to about 90° of flexion, the first portion being generally arcuate and having a radius extending from a center spaced in a first transverse direction from the sagittal plane.

10. The improvement of claim 9 wherein the predetermined curvature of each prescribed track includes a second portion extending from a location corresponding to about 90° of flexion to a location corresponding to about 150° of flexion, the second portion being generally arcuate and having a radius extending from a center spaced in a second transverse direction from the sagittal plane, the second transverse direction being opposite to the first transverse direction.

11. The improvement of claim 7 wherein relative rotation about the longitudinal axis of rotation is enabled up to about 5° of relative rotation, during flexion up to about 90° of flexion.

12. The improvement of claim 7 wherein relative rotation about the longitudinal axis of rotation is enabled up to about 5° of relative rotation, during flexion up to about 150° of flexion.

* * * * *